(12) United States Patent
Ciurczak et al.

(10) Patent No.: US 6,534,768 B1
(45) Date of Patent: Mar. 18, 2003

(54) HEMISPHERICAL DETECTOR

(75) Inventors: Emil W. Ciurczak, Goldens Bridge, NY (US); Kevin C. Bynum, Yonkers, NY (US)

(73) Assignee: Euro-Oeltique, S.A., Luxembourg (LU)

( * ) Notice: Subject to any disclaimer, the term of this patent is extended or adjusted under 35 U.S.C. 154(b) by 18 days.

(21) Appl. No.: 09/699,702

(22) Filed: Oct. 30, 2000

(51) Int. Cl.⁷ .............................. G01J 5/28; G01J 5/10
(52) U.S. Cl. ........................ 250/339.02; 250/339.07; 250/379.11; 250/339.12; 250/341.8; 250/343
(58) Field of Search ..................... 250/339.02, 332, 250/339.07, 339.11, 339.12, 341.8, 343

(56) References Cited

U.S. PATENT DOCUMENTS

| | | | |
|---|---|---|---|
| 3,531,202 A | 9/1970 | Wilkinson et al. | 356/81 |
| 3,627,421 A | 12/1971 | Harley | 356/98 |
| RE28,221 E | 11/1974 | Beenghiat | 340/172.5 |
| 3,846,024 A | 11/1974 | Turner | 356/80 |
| 3,973,849 A | 8/1976 | Jackson et al. | 365/97 |
| 3,983,965 A | 10/1976 | Wright | 188/1 |
| 4,012,147 A | 3/1977 | Walrafen | 365/98 |
| 4,060,327 A | 11/1977 | Jacobowitz et al. | 356/96 |
| 4,100,416 A | 7/1978 | Hirschfeld | 250/461 |
| 4,101,222 A | 7/1978 | Mathisen | 356/244 |
| 4,103,760 A | 8/1978 | Yang | 188/1 |
| 4,105,098 A | 8/1978 | Klimaitits | 188/1 |
| 4,146,332 A | 3/1979 | Moore | 356/308 |
| 4,185,720 A | 1/1980 | Wright et al. | 188/134 |
| 4,192,173 A | 3/1980 | Ay et al. | 73/11 |
| 4,198,849 A | 4/1980 | Siess et al. | 73/1 F |
| 4,205,229 A | 5/1980 | Beer | 250/352 |
| 4,240,751 A | 12/1980 | Linnecke et al. | 356/409 |
| 4,260,528 A | 4/1981 | Fox et al. | 252/525 |
| 4,275,963 A | 6/1981 | Primbsch | 356/35.5 |
| 4,285,596 A | 8/1981 | Landa | 356/308 |
| 4,330,210 A | 5/1982 | Hashimoto et al. | 356/328 |
| 4,342,516 A | 8/1982 | Chamran et al. | 356/332 |
| 4,357,673 A | 11/1982 | Willis et al. | 364/582 |
| 4,407,008 A | 9/1983 | Schmidt et al. | 358/93 |
| 4,412,744 A | 11/1983 | Lee et al. | 356/319 |
| 4,458,323 A | 7/1984 | Willis et al. | 364/582 |
| 4,509,856 A | 4/1985 | Lee | 356/246 |
| 4,536,091 A | 8/1985 | Allington | 356/435 |
| 4,544,271 A | 10/1985 | Yamamoto | 356/328 |
| 4,567,370 A | 1/1986 | Falls | 250/461.1 |
| 4,583,187 A | 4/1986 | Stoub | 364/571 |
| 4,650,336 A | 3/1987 | Moll | 356/417 |
| 4,675,529 A | 6/1987 | Kushida | 250/458.1 |
| 4,675,581 A | 6/1987 | Dietz | 315/398 |
| 4,676,640 A | 6/1987 | Briggs | 356/317 |
| 4,685,801 A | 8/1987 | Minekane | 356/328 |
| 4,699,510 A | 10/1987 | Alguard | 356/73 |
| 4,707,056 A | 11/1987 | Bittner | 350/96.12 |
| 4,800,279 A | 1/1989 | Hieftje et al. | 250/339 |
| 4,837,439 A * | 6/1989 | Genna et al. | 250/363.04 |

(List continued on next page.)

OTHER PUBLICATIONS

Burns & Ciurczak, Handbook of Near–Infrared Analysis, pp 42–43 (1992).

*Primary Examiner*—Constantine Hannaher
*Assistant Examiner*—Albert Gagliardi
(74) *Attorney, Agent, or Firm*—Davidson, Davidson & Kappel, LLC

(57) ABSTRACT

A hemispherical detector comprising a plurality of photodetectors arranged in a substantially contiguous array, the array being substantially in the shape of a half-sphere, the half-sphere defining a closed end and an open end, the open end defining a substantially circular face. Also provided is a method for constructing a hemispherical detector comprising the steps of making a press mold of the desired shape of the hemispherical detector, pouring a material into the press mold to form a cast, finishing the cast to remove any defects, coating the cast with a coating material, and attaching a plurality of photodetectors to the cast.

45 Claims, 14 Drawing Sheets

U.S. PATENT DOCUMENTS

| | | | |
|---|---|---|---|
| 4,867,562 A | 9/1989 | Oishi et al. | 356/312 |
| 4,882,493 A | 11/1989 | Lodder et al. | 250/353 |
| 4,883,963 A | 11/1989 | Kemeny et al. | 250/339 |
| 4,916,309 A * | 4/1990 | Keane | 250/227.29 |
| 4,936,684 A | 6/1990 | Keane | 356/328 |
| 4,972,866 A | 11/1990 | Anthony et al. | 137/110 |
| 4,975,581 A | 12/1990 | Robinson et al. | 250/339 |
| 4,989,932 A | 2/1991 | Landa et al. | 350/96.1 |
| 5,003,500 A | 3/1991 | Gerber | 364/526 |
| 5,040,889 A | 8/1991 | Keane | 356/51 |
| 5,044,747 A | 9/1991 | Anthony | 356/246 |
| 5,044,755 A | 9/1991 | Landa et al. | 356/440 |
| 5,072,109 A * | 12/1991 | Aguilera et al. | 250/226 |
| 5,095,205 A | 3/1992 | Schleicher et al. | 250/226 |
| 5,104,220 A | 4/1992 | Okumoto et al. | 356/307 |
| 5,116,123 A | 5/1992 | Kuderer | 356/326 |
| 5,166,756 A | 11/1992 | McGee et al. | 356/446 |
| 5,200,818 A * | 4/1993 | Neta et al. | 348/36 |
| 5,227,856 A | 7/1993 | Reed et al. | 356/402 |
| 5,313,542 A * | 5/1994 | Castonguay | 250/227.28 |
| 5,349,188 A | 9/1994 | Maggard | 250/339 |
| 5,483,337 A | 1/1996 | Barnard et al. | 356/316 |
| 5,545,376 A | 8/1996 | Honigs et al. | 422/104 |
| 5,694,206 A | 12/1997 | Curtiss | 356/72 |
| 5,729,333 A | 3/1998 | Osten et al. | 356/39 |
| 5,731,874 A | 3/1998 | Maluf | 356/326 |
| 5,739,527 A * | 4/1998 | Hecht et al. | 250/216 |
| 5,739,537 A | 4/1998 | Siesler et al. | 250/341.8 |
| 5,747,806 A | 5/1998 | Khalil et al. | 250/339.12 |
| 5,763,884 A | 6/1998 | Hammond et al. | 250/339.11 |
| 5,822,219 A | 10/1998 | Chen et al. | 364/498 |
| 5,867,562 A | 2/1999 | Scherer | 379/88 |
| 5,880,831 A | 3/1999 | Buermann et al. | 356/319 |
| 5,883,823 A | 3/1999 | Ding | 364/725.03 |
| 5,991,022 A | 11/1999 | Buermann et al. | 356/319 |
| 5,996,288 A | 12/1999 | Aiken | 52/81.3 |
| 6,005,661 A | 12/1999 | Machler | 356/326 |
| 6,014,212 A | 1/2000 | Hammond et al. | 356/319 |
| 6,031,233 A | 2/2000 | Levin et al. | 250/339.11 |
| 6,037,590 A * | 3/2000 | Boreman et al. | 250/338.1 |
| 6,064,067 A * | 5/2000 | Zhao et al. | 250/227.28 |
| 6,236,050 B1 * | 5/2001 | Tumer | 250/363.03 |

\* cited by examiner

Near-infared Transmittance (NIT)

Near-infared Reflectance (NIR)

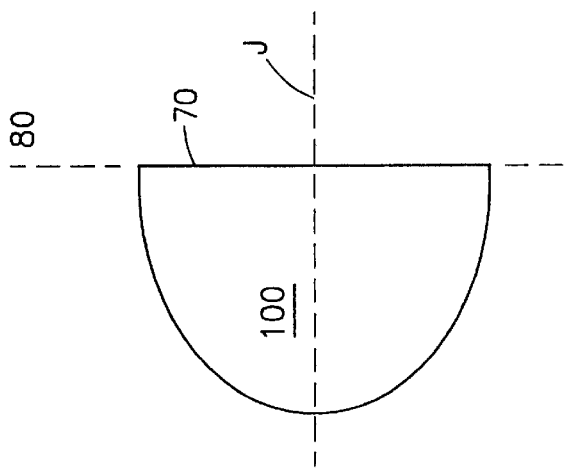
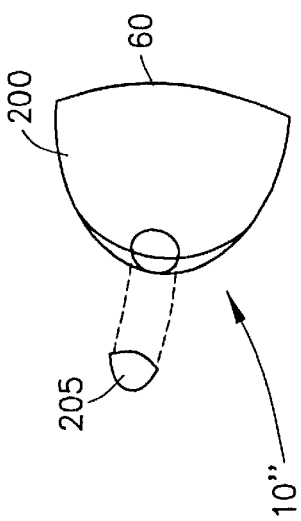
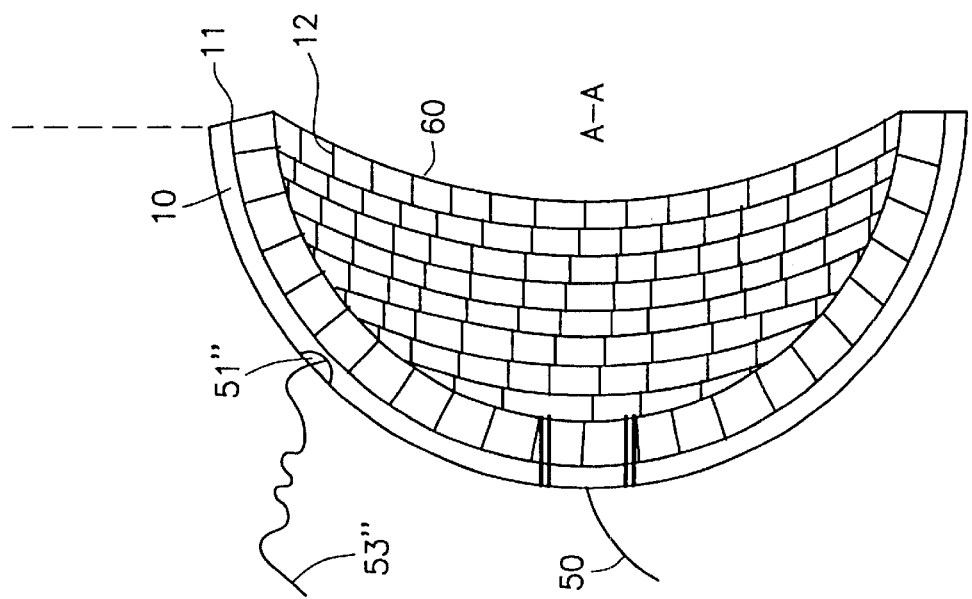
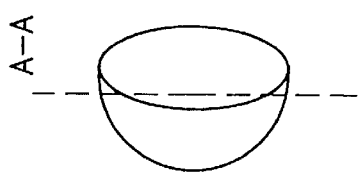
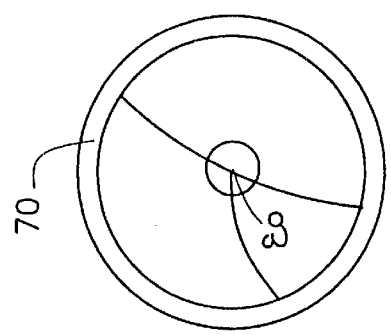

HEMISPHERICAL DETECTOR

FIELD OF THE INVENTION

The present invention relates to the field of spectroscopic detectors. Specifically, the present invention relates to a hemispherical detector for use with a transmittance or reflectance spectrometer which comprises a plurality of photodetectors.

BACKGROUND OF THE INVENTION

Infrared spectroscopy is a technique which is based upon the vibrations of the atoms of a molecule. In accordance with infrared spectroscopy, an infrared spectrum is generated by transmitting radiation through a sample and determining what portion of the incident radiation is absorbed by the sample at a particular energy. Near infrared radiation is radiation having a wavelength between about 700 nm and about 2500 nm.

In general spectrometers (e.g., a spectrophotometer) can be divided into two classes: transmittance spectrometers and reflectance spectrometers. In a transmittance spectrometer, light having a desired narrow band of wavelengths is directed onto a sample, and a detector detects the light which was transmitted through the sample. In contrast, in a reflectance spectrometer, light having a narrow band of wavelengths is directed onto a sample and one or more detectors detect the light which was reflected off of the sample. Depending upon its design, a spectrometer may, or may not, be used as both a transmittance and a reflectance spectrometer.

A variety of different types of spectrometers are known in the art such as grating spectrometers, FT (Fourier transformation) spectrometers, Hadamard transformation spectrometers, AOTF (Acousto Optic Tunable Filter) spectrometers, multiple discrete wavelength source spectrometers, filter-type spectrometers, scanning dispersive spectrometers, and double-beam spectrometers.

Filter-type spectrometers, for example, utilize a light source (such as a conventional light bulb) to illuminate a rotating opaque disk, wherein the disk includes a number of narrow bandpass optical filters. The disk is then rotated so that each of the narrow bandpass filters passes between the light source and the sample. An encoder indicates which optical filter is presently under the light source. The filters filter the light from the light source so that only a narrow selected wavelength range passes through the filter to the sample. Optical detectors are positioned to detect light which either is reflected by the sample (to obtain a reflectance spectra) or is transmitted through the sample (to generate a transmittance spectra). The amount of detected light is then measured, which provides an indication of the amount of absorbance of the light by the substance under analysis.

Multiple discrete wavelength source spectrometers use infrared emitting diodes (IREDs) as sources of near-infrared radiation. A plurality (for example, eight) of IREDs are arranged over a sample work surface to be illuminated for quantitative analysis. Near-infrared radiation emitted from each IRED impinges upon an accompanying optical filter. Each optical filter is a narrow bandpass filter which passes NIR radiation at a different wavelength. NIR radiation passing through the sample is detected by a detector (such as a silicon photodetector). The amount of detected light is then measured, which provides an indication of the amount of absorbance of the light by the substance under analysis. IRED reflectance spectroscopy is also possible.

Acousto Optic Tunable Filter spectrometers utilize an RF signal to generate acoustic waves in a $TeO_2$ crystal. A light source transmits a beam of light through the crystal, and the interaction between the crystal and the RF signal splits the beam of light into three beams: a center beam of unaltered white light and two beams of monochromatic and orthogonally polarized light. A sample is placed in the path of one of the monochromatic beams and detectors are positioned to detect light which either is reflected by the sample (to obtain a reflectance spectra) or is transmitted through the sample (to generate a transmittance spectra). The wavelength of the light source is incremented across a wavelength band of interest by varying the RF frequency. The amount of detected light is then measured, which provides an indication of the amount of absorbance of the light by the substance under analysis.

In grating monochrometer spectrometers, a light source transmits a beam of light through an entrance slit and onto a grating element (the dispersive element) to disperse the light beam into a plurality of beams of different wavelengths (i.e., a dispersed spectrum). The dispersed light is then reflected back through an exit slit on to a detector. By selectively altering the path of the dispersed spectrum relative to the exit slit, the wavelength of the light directed to the detector can be varied. The amount of detected light is then measured, which provides an indication of the amount of absorbance of the light by the substance under analysis. The width of the entrance and exit slits can be varied to compensate for any variation of the source energy with wavenumber. This approach lends itself to reflectance spectrometry.

Dual-beam spectrometers split radiation from a source into two beams, half passing into a sample-cell compartment and the other half into a reference area. The reference beam then passes through an attenuator and on to a chopper, which is a motor-driven disk that alternatively reflects the reference or transmits the beam to a detector. After dispersion by a prism or grating, the sample-cell beam passes to the sample and a detector detects the transmittance that passes through the sample or reflectance that reflects from the sample. If the two beams are identical in power, the detectors transmit similar electrical signals to a null detector. The null detector in turn produces an unfluctuating direct current. However, if the two beams differ in power, the detectors transmit differing electrical signals to the null detector. In this case, the null detector produces a fluctuating electrical current, which is used to generate the spectral data. For example, the fluctuating current can be used to drive a synchronous motor in one direction or the other depending upon the phase of the current; with the synchronous motor mechanically linked to a pen drive of a recorder, which the synchronous motor causes to move to generate the spectral data. This approach lends itself to both transmittance and reflectance spectrometry.

Detectors used in spectroscopy generally fall into two classes, photographic detectors, in which radiation impinges upon an unexposed photographic film, and electronic detectors, in which the radiation impinges upon a detector and is converted into an electrical signal. Electronic detectors provide the advantage of increased speed and accuracy, as well as the ability to convert the spectral data into an electronic format, which can be displayed, processed, and/or stored. Examples of electronic detectors include photomultiplier tubes and photodetectors. Photomultiplier tubes are quite sensitive, but are relatively large and expensive. Photodetectors provide the advantage of reduced size and cost. These detectors include IR detectors, pin diode detectors, charge coupled device detectors, and charge injection device detectors.

Conventionally, spectroscopic detectors are configured either as a single detector, flat detector, or a plurality of discrete detectors arranged in common plane (e.g. a flat array). In either case, these "flat" detector arrangements inherently detect only a 3% portion of the transmitted or reflected spectral data for 1 cm$^2$ detectors at a 2 cm distance from the source detector.

As described in Burns & Ciurczak, HANDBOOK OF NEAR-INFRARED ANALYSIS, pp 42–43 (1992), detectors for measuring diffuse reflectance are known which include either two or four opposing detectors arranged at a 45 degree angle from the sample. In general, PbS detectors are used for measurements in the 1100–2500-nm region, whereas PbS "sandwiched" with silicon photodiodes are most often used for visible-near-infrared applications (typically 400–2600 nm).

The signal from the detectors is added to a low-noise, high-gain amplifier and then converted from analog to digital. The digital signal is exported from the instrument to an on-board or external microcomputer for data processing, calibration, and storage. The computer records a signal representing the actual wave-length used for measurement with the raw reflectance or transmittance digital data. This function is repeated for both the sample and the reference. The spectrum, then, is the difference between the raw reflectance measurement of the sample and the raw reflectance measurement of the reference material. Raw reflectance is converted to absorbance using the function Absorbance=–log (10)* Reflectance, commonly referred to as log 1/R. Raw transmittance is converted to absorbance using the expression log 1/T.

SUMMARY OF THE INVENTION

When configured with four opposing 1 cm$^2$ detectors at 45 degree angles and 2 cm from the sample, the diffuse reflectance detector described above provides the advantage of collecting spectral data from four different vantage points, as compared to more conventional "flat" detector arrangements. However, even with this configuration, only about 12% of the reflected spectral data is detected. Moreover, this configuration is not suitable for use with a transmittance spectrometer.

In accordance with a first embodiment of the present invention, a hemispherical detector for use with a transmittance spectrometer is provided which comprises a plurality of photodetectors arranged in a substantially contiguous array, the array being substantially in the shape of a half-sphere, the half-sphere defining a closed end and an open end, the open end defining a substantially circular face. In use, a sample to be analyzed preferably intersects a plane passing through the substantially circular face, and a transmitted beam of light from the transmittance spectrometer intersects the plane at a 90 degree angle to, and at a center-point of, said substantially circular face. In this manner, substantially all of the light which passes through the sample is detected by the detector array. Currently, most photodetectors have a flat surface. Therefore, the individual photodetectors which comprise the array of photodetectors are preferably about 0.5–3 mm$^2$ in order to provide a substantially spherical shape. If available, smaller photodetectors can also be used. In this manner, except for beams of light which strike between photodetectors, all of the light which passes through the sample is detected by the photodetector array. In this regard, it is believed that this configuration can detect about 80% of the spectral data.

In accordance with a second embodiment of the present invention, a hemispherical detector for use with a reflectance spectrometer is provided which comprises a plurality of photodetectors arranged in a substantially contiguous array, the array being substantially in the shape of a truncated half-sphere, the truncated half-sphere defining a first open end and a second open end, the second open end defining a substantially circular face having a diameter ("d"), the first open end having a cutout formed therein, wherein the cutout defines an area which is less than $\Pi (d/2)^2$. In use, a sample to be analyzed preferably intersects a plane passing through the substantially circular face, and a transmitted beam of light from the reflectance spectrometer passes through the second open end in a direction perpendicular to the plane and co-axial with a center-point of said substantially circular face. In this manner, substantially all of the light which reflects off of the sample is detected by the detector array. As with the first embodiment described above, the individual photodetectors which comprise the array of photodetectors are preferably about 0.5–3 mm$^2$ in order to provide a substantially spherical shape. In this manner, except for beams of light which strike between photodetectors, or are reflected back through the first open end, all of the light which is reflected off of the sample is detected by the photodetector array. Preferably, the area of the opening defined by the first open end is minimized in order to maximize the percentage of the reflected light which is received by the detector arrays. However, the opening must remain sufficiently large to allow the transmitted beam of light to impinge upon the sample. Also, motion due to the operation of the spectrometer may cause the shell of the detector to infringe the path of the beam of light. Most preferably, the first open end is a circular cut-out having a diameter of approximately 5 mm.

In accordance with a third embodiment of the present invention, a hemispherical detector for use with a reflectance or transmittance spectrometer is provided which comprises a plurality of photodetectors arranged in a substantially contiguous array, the array being substantially in the shape of a half-sphere. The half-sphere includes a first portion and a second portion. The first portion is in the shape of a truncated half sphere, the truncated half sphere defining a first open end and a second open end, the second open end defining a substantially circular face having a diameter ("d"), the first open end having a cutout formed therein, wherein the cutout defines an area which is less than $\Pi (d/2)^2$. The second portion is removably secured to the first open end. When performing a transmittance measurement, the second portion is secured to the first portion, thereby forming photodetector array which is substantially in the shape of a half-sphere. The hemispherical detector can then be used in the manner described above with reference to the first embodiment. In order to perform a reflectance measurement, the second portion is removed from the first portion, thereby forming photodetector array which is substantially in the shape of a truncated half-sphere. The hemispherical detector can then be used in the manner described above with reference to the second embodiment.

It is believed that the detectors of the second and third embodiment, like the first embodiment, can detect approximately 80% of the spectral data.

In each of the embodiments described above, openings are preferably provided in the shell to allow wires to contact the photodetectors. This prevents the wires from interfering with data acquisition.

The detectors in accordance with the present invention may be used in a variety of spectrometers including, for example, filter-type spectrometers, multiple discrete wavelength source spectrometers, AOTF (Acousto Optic Tunable Filter) spectrometers, grating spectrometers, FT (Fourier transformation) spectrometers, Hadamard transformation spectrometers, post-dispersive monochrometer spectrometers, double beam spectrometers, and scanning dispersive spectrometers. In these embodiments the detectors provide the advantage of a more accurate measurement by increasing the percentage of spectral data which is detected.

In the embodiments described above, the substantially circular face preferably has a diameter of from about 1.5 mm to about 1 m.

The hemispherical detectors in accordance with the present invention may be constructed in a number of ways.

For example, the hemispherical detector may be constructed by a mold method. In accordance with this method, a press mold is created, a material is poured into the mold to create a cast (which forms the shell of the detector) and a plurality of photodetectors are attached to the cast. This has the advantage of quick and efficient construction. Moreover, a plurality of uniform hemispherical detectors may be made. The cast preferably has a diameter of from about 1.5 mm to about 1 m.

The hemispherical detector may also be constructed by an airform method. In accordance with this method, a malleable airform, e.g., plastic, may be fabricated to the proper shape and size, inflated, and then coated with a hardening material to create the shell of the detector. This has the advantage of a strong and stable hemispherical detector at a marginal cost. Also, this method provides the advantage that detectors of differing sizes can easily be constructed by modifying the amount of material in the airform. The malleable airform preferably has a diameter of from about 1.5 mm to about 1 m.

The hemispherical detector may also be constructed by geodesic dome method. In accordance with this method, a plurality of pentagons, hexagons, and half hexagons are joined together in a geodesic dome shape, e.g., such that every pentagon is surrounded by 5 hexagons, half-hexagons, or combination thereof. Photodetectors or fillings with photodetectors attached may be secured in the areas between the struts. This has the advantage of a versatile and sturdy construction. The geodesic dome shape preferably has a diameter of from about 1.5 mm to 1 m. Moreover, as six struts could form the entire circumferential length of the dome, each strut preferably has a length of from about 0.39 mm to 0.26 m.

Preferably, the ceramic mold, airform, or geodesic dome hemispherical detector construction method may be further modified to allow for additional wiring. In this regard, apertures may be drilled in the hemispherical detector to allow wiring to contact the photodetector.

Although the above-referenced methods of construction are preferred, other methods known in the art may alternatively be used.

BRIEF DESCRIPTION OF THE DRAWINGS

FIG. 4(a) is a side perspective view of a detector in accordance with a third embodiment of the present invention which is suitable for use with both a transmittance and a reflectance spectrometer, the detector being in the shape of a half sphere.

FIG. 4(b) is a side view of the detector of FIG. 4(a), illustrated as a cross-section through a line A—A, which bisects the half sphere.

FIG. 4(c) is a side view of the detector of FIG. 4(a).

FIG. 4(d) is a front view of the detector of FIG. 4(a).

FIG. 4(e) is an exploded rear perspective view of the detector of FIG. 4(a) showing the first and second portions disengaged.

DETAILED DESCRIPTION OF THE PREFERRED EMBODIMENTS

FIGS. 1 (a–b) show the two most prevalent basic instrument designs common in modern near-infrared analysis; a transmittance spectrometer and reflectance spectrometer.

Figure 1A:
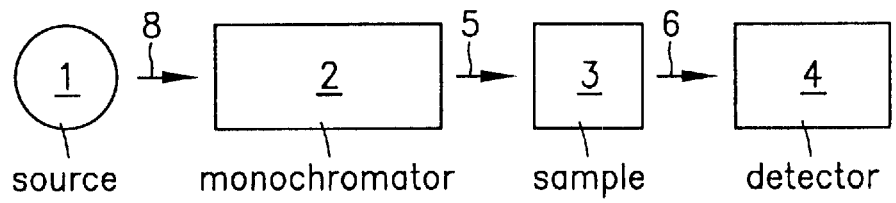
FIG. 1(a) illustrates a common instrument design for a transmittance spectrometers.
Figure 1B:
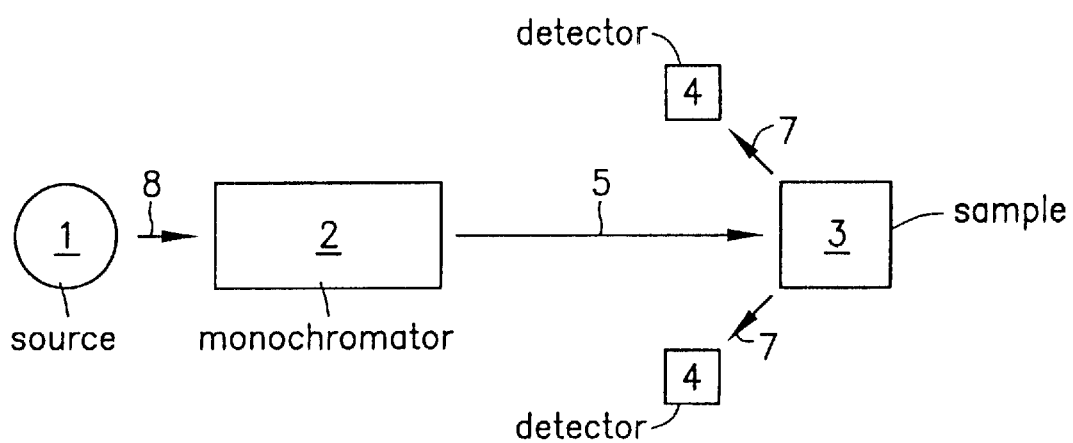
FIG. 1(b) illustrates a common instrument design for a reflectance spectrometer.
Figure 2B:
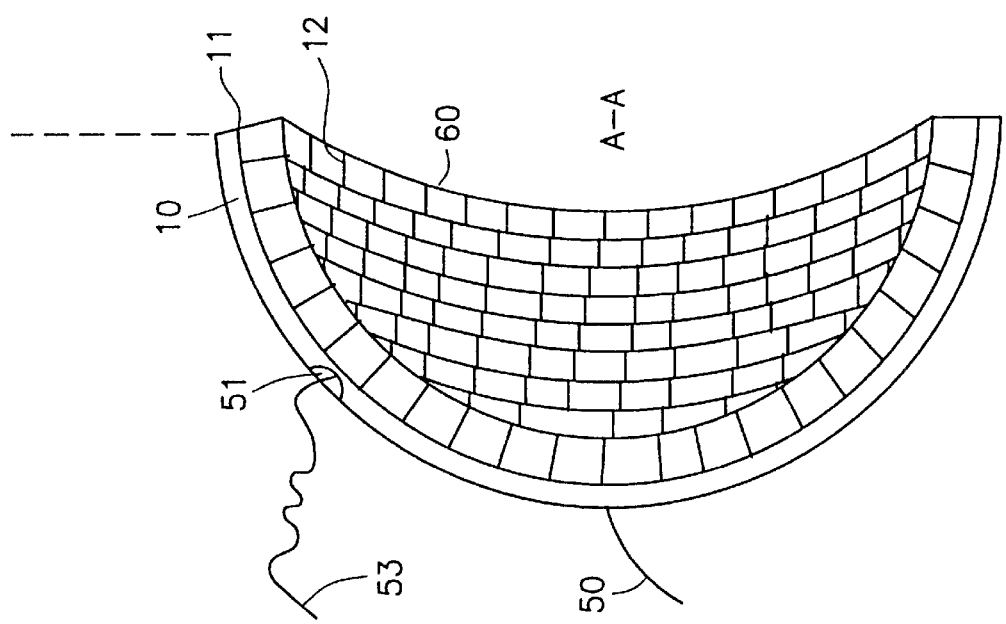
FIG. 2(b) is a side view of the detector of FIG. 2(a), illustrated as a cross-section through a line A—A, which bisects the half sphere.
Figure 2C:
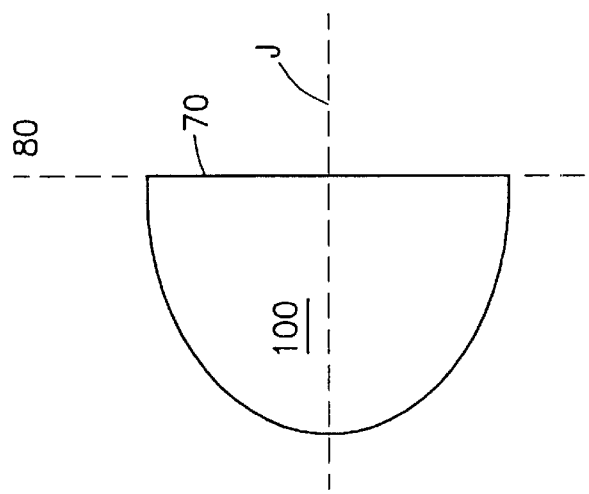
FIG. 2(c) is a side view of the detector of FIG. 2(a).
Figure 2A:
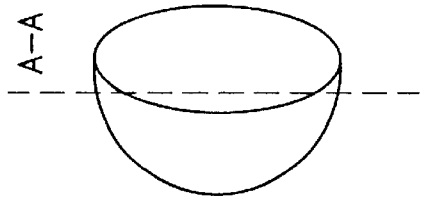
FIG. 2(a) is a side perspective view of a detector in accordance with a first embodiment of the present invention which is suitable for use with a transmittance spectrometer, the detector being in the shape of a half sphere.
Figure 2D:
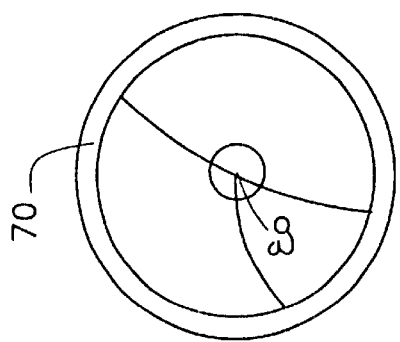
FIG. 2(d) is a front view of the detector of FIG. 2(a).
Figure 3C:
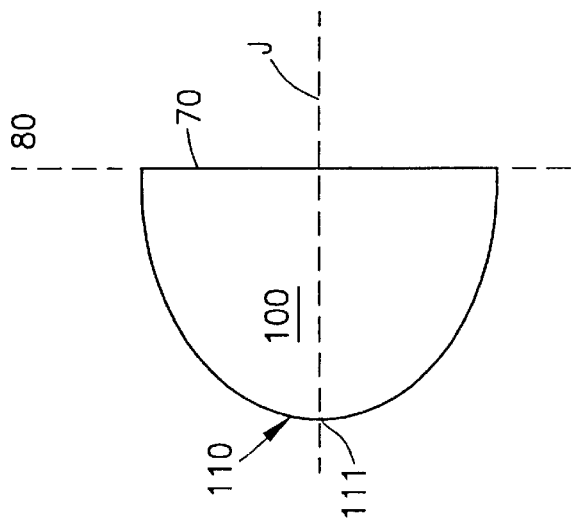
FIG. 3(c) is a side view of the detector of FIG. 3(a).
Figure 3E:
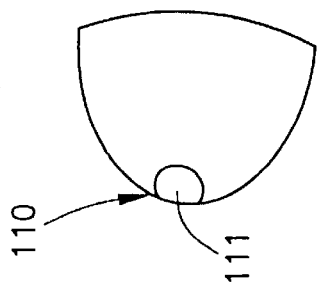
FIG. 3(e) is a rear perspective view of the detector of FIG. 3(a).
Figure 3B:
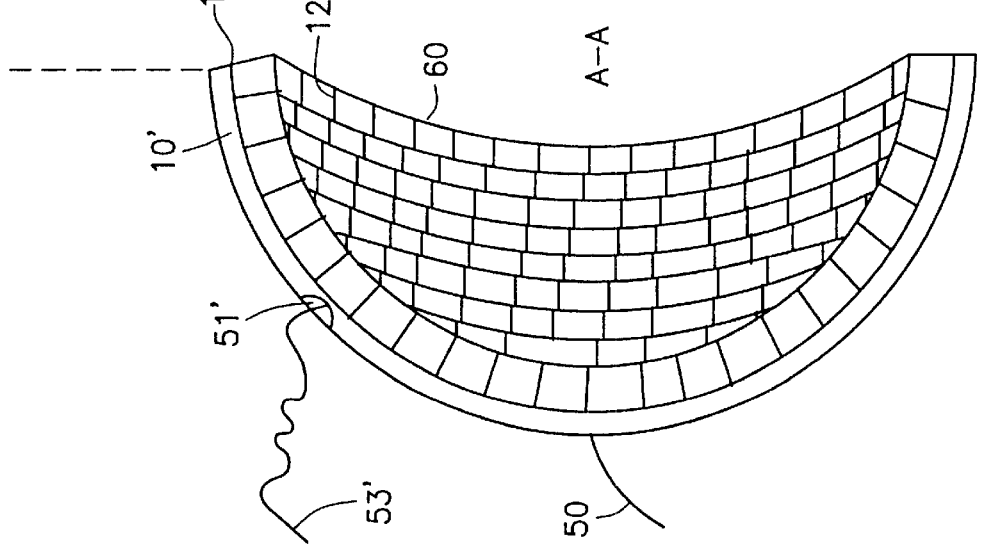
FIG. 3(b) is a side view of the detector of FIG. 3(a), illustrated as a cross-section through a line A—A, which bisects the truncated half sphere.
Figure 3A:
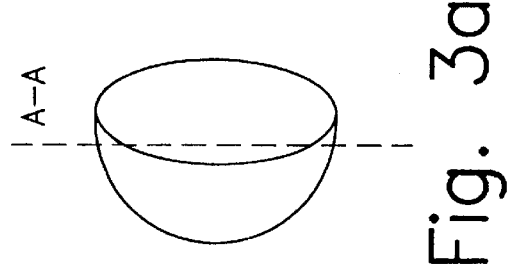
FIG. 3(a) is a side perspective view of a detector in accordance with a second embodiment of the present invention which is suitable for use with a reflectance spectrometer, the detector being in the shape of a truncated half sphere.
Figure 3D:
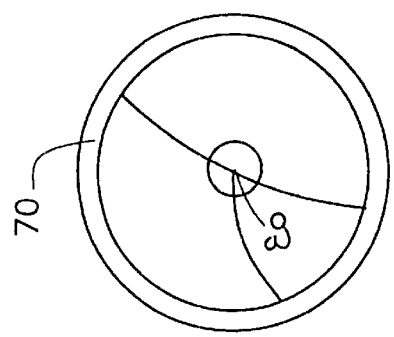
FIG. 3(d) is a front view of the detector of FIG. 3(a).

FIG. 1(a) shows a transmittance spectrophotometer and FIG. 1(b) shows a reflectance spectrometer. In both cases, a monochrometer 2 produces a light beam 5 having desired narrow band of wavelengths from light 8 emitted from a light source 1, and the light beam 5 is directed onto a sample 3. However, in the case of a transmittance spectrometer, a plurality of detectors 4 are positioned to detect the light 6 which is transmitted through the sample 3, and in the case of a reflectance spectrometer, the plurality of detectors 4 are positioned to detect a reflected light beam 7 which is reflected off the sample 3. Depending upon its design, a spectrometer may, or may not, be used as both a transmittance and a reflectance spectrometer.

Reflectance measurements penetrate only 1–4 mm of the front surface of ground samples. This small penetration of energy into a sample brings about greater variation when measuring nonhomogeneous samples than transmittance techniques.

In transmittance measurements, the entire path length of the sample is integrated into the spectral measurement, thereby reducing errors due to non-homogeneity of samples. Transmittance techniques are most useful for measuring large particles. For fine particles, the front surface scatter brings about a loss of energy transmitted through a sample, with the net effect being a decrease in the signal-to-noise of the instrument. In transmittance, higher frequency energy is most commonly used due to its greater depth of penetration into the sample. The higher frequency energy (800–1400 nm) is more susceptible to front surface scattering than lower frequency energy.

Transmittance measurements should therefore be optimized taking into consideration the relationships between the frequency used for measurement, front surface scatter, and the path length of the sample. In transmittance measurements, particle size can be small enough to begin to scatter most of the energy striking the sample. If the particle size is sufficiently small, the instrument will not transmit enough energy through the sample for the detectors to record a signal. To compensate, a preferred spectrophotometer would have both transmittance and reflectance capabilities.

FIGS. 2(a–d) shows a hemispherical detector in accordance with a first embodiment of the present invention for use with a transmittance spectrometer. The detector includes a plurality of photodetectors 12 arranged in a substantially contiguous array. The photodetectors may, for example, be InAs photon detectors, InSb photon detectors, PbS photon detectors, PbSe photon detectors, or InGaAs photon detectors. The particular photodetector used is dictated by the anticipated application. For example, InAs, InSb, PbS, and PbSe photon detectors are generally used for infrared applications, whereas InGaAs, PbS, and InAs photon detectors are generally used for near-infrared applications. The photodetectors may also be, for example, photoconductive photon detectors; PbSi photoconductive photon detectors; photvoltaic photon detectors; photodiodes; Si, Thermoelectrically-cooled Si, GaP, GaAsP, or InGaAs photodiodes; PbS photodiodes sandwiched with Si photodiodes; photoconductive cells; Cds or PbSe/PbS photoconductive cells; and InAs/InSb photovoltaic detectors. Ge photodetectors may also be used. The array may be comprised of a single type of photodetector, or, alternatively, two or more different types of photodetectors may be used. Moreover, the array may include photodetector clusters (i.e., two or more different types of photodetectors fabricated as a single unit or cluster).

The photodetectors 12 arranged in a substantially contiguous array are supported on a shell 10 which has an inner surface 11, which is configured to hold the photodetectors 12 arranged in a substantially contiguous array substantially in the shape of a half sphere. The half-sphere defines a closed end 50 and an open end 60. The open end 60 defines a substantially circular face 70. In use, a sample to be analyzed preferably intersects a plane 80 passing through the substantially circular face 70, and the transmitted beam of light 5 from the transmittance spectrometer (FIG. 1A) intersects the plane at a 90 degree angle, and at a center-point 90 of said substantially circular face 70. In this manner, substantially all of the light which passes through the sample is detected by the photodetectors 12 arranged in a substantially contiguous array. Currently, photodetectors have a flat surface. Therefore, the individual photodetectors which comprise the array of photodetectors are preferably about 0.5–3 mm$^2$ in order to provide a substantially spherical shape. In this manner, except for beams of light which strike between photodetectors, all of the light which passes through the sample is detected by the photodetector array.

Openings 51 are provided in the shell 10 to allow wires 53 to contact the photodetectors 12. This prevents the wires 53 from interfering with data acquisition.

FIGS. 3(a–e) show a hemispherical detector for use with a reflectance spectrometer, with similar components bearing like reference numerals to FIGS. 2(a–c). The detector includes the plurality of photodetectors 12' arranged in a substantially contiguous array. The plurality of photodetectors 12' arranged in a substantially contiguous array are supported on a shell 10' which has an inner surface 11' which is configured to hold the photodetectors 12' arranged in a substantially contiguous array substantially in the shape of a truncated half-sphere. The truncated half-sphere defines a first open end 110 and a second open end 60'. The second open end 60' defines the substantially circular face 70' as having a diameter ("d"). The first open end 110 has a cutout 111 formed therein, wherein the cutout defines an area which is less than $\Pi (d/2)^2$. In use, a sample to be analyzed preferably intersects the plane 80' passing through the substantially circular face 70', and a transmitted beam of light 5' from the reflectance spectrometer (FIG. 1b) passes through the second open end 60' in a direction perpendicular to the plane 80' and co-axial with a center-point 90' of said substantially circular face 70'. In this manner, substantially all of the light which reflects off of the sample is detected by the plurality of photodetectors 12' arranged in a substantially contiguous array. As with the first embodiment described above, the individual photodetectors which comprise the array of photodetectors are preferably about 0.5–3 mm$^2$ in order to provide a substantially spherical shape. In this manner, except for beams of light which strike between photodetectors, or are reflected back through the first open end, all of the light which is reflected off of the sample is detected by the photodetector array. Preferably, the area of the cut-out 111 is minimized in order to maximize the percentage of the reflected light which is received by the detector array. The cut-out should, however, be large enough to allow the beam of lights to reach the sample. Most preferably, the cut-out 111 is a circular cut-out having a diameter of approximately 5 mm.

Openings 51' are provided in the shell 10' in order to allow wires 53' to contact the photodetectors 12'.

FIGS. 4(a–e) show a hemispherical detector for use with a reflectance or transmittance spectrometer, with similar components bearing like reference numerals to FIGS. 2(a–d). The detector includes the plurality of photodetectors 12" arranged in a substantially contiguous array. The photodetectors 12" arranged in a substantially contiguous array are supported on a two part shell 10" which has an inner surface 11" which is configured to hold the plurality of photodetectors 12" arranged in a substantially contiguous array substantially in the shape of a half-sphere. The shell 10" includes a first portion 200 and a second portion 205. The first portion 200 is in the shape of a truncated half sphere. The truncated half sphere defines a first open end 10' and a second open end 60", the second open end 60" defining a substantially circular face having a diameter ("d"). The first open end 110' has a cutout 111' formed therein, wherein the cutout defines an area which is less than $\Pi (d/2)^2$. As shown in FIG. 4(e), the second portion 205 is removably secured to the first open end 110'. In this regard, the second portion 205 could be removably secured to the second open end: via a friction fit; by providing respective threads on the first and second portion; utilizing a latch mechanism; or in any other manner known to one of skill in the art.

When performing a transmittance measurement, the second portion 205 is secured to the first portion 200, thereby forming photodetector array which is substantially in the shape of a half-sphere. The hemispherical detector can then be used in the manner described above with reference to the FIGS. 2(a–d). In order to perform a reflectance measurement, the second portion 205 is removed from the first portion 200, thereby forming the photodetector 12" arranged in a substantially contiguous array which is substantially in the shape of a truncated half-sphere. The hemispherical detector can then be used in the manner described above with reference to FIGS. 3(a–e).

Openings are 51" are provided in the shell 10" in order to allow wires 53" to contact the photodetectors 12".

Figure 4F:
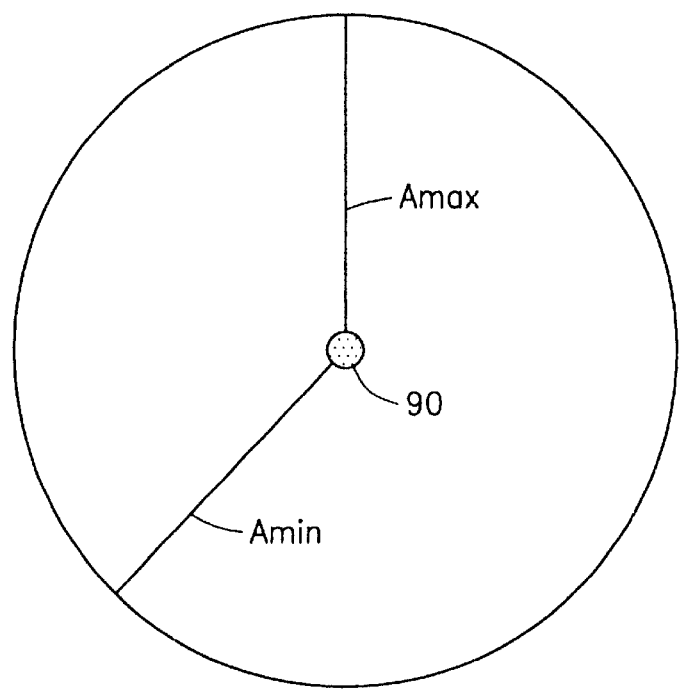
FIGS. 4(f) and 4(g) illustrate the relative dimensions of a hemispherical detector which is substantially in the shape of a half sphere or substantially in the shape of a truncated half sphere.
Figure 4G:
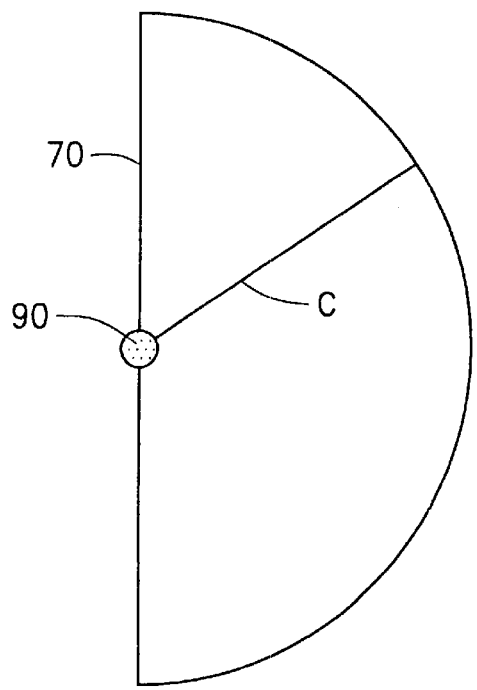

As set forth above, the hemispherical detectors in accordance with FIGS. 2, 3, and 4 include photodetectors arranges in an array which is substantially in the shape of sphere or half sphere. Referring to FIGS. 4(f) and 4(g), in accordance with the present invention, a array is considered substantially in the shape of a half sphere or truncated half sphere: i) if a ratio of a minimum radius (Amin) and a maximum radius (Amax) of the face 70 of the sphere or truncated sphere (from the centerpoint 90) is equal to Amin/Amax= 1+/−0.1; and if the distance b from the centerpoint 90 on the face 70 to any point on the array is equal to b=(Amin+Amax)/2+/−0.1*((Amin+Amax)/2). It should be noted, moreover that although the shell 50 is illustrated as being in the shape of a sphere or half-sphere, the shell 50 can, of course, have a different shape provided that the photodetector array is substantially in the shape of a half sphere or truncated half sphere.

The detectors in accordance with the present invention may be used with a variety of spectrometers including, for example, filter-type spectrometers, multiple discrete wavelength source spectrometers, AOTF (Acousto Optic Tunable Filter) spectrometers, grating spectrometers, FT (Fourier transformation) spectrometers, Hadamard transformation spectrometers, post-dispersive monochrometer spectrometers, double beam spectrometers, and scanning dispersive spectrometers.

The wires 53 shown in FIGS. 2, 3 and 4 may be connected to one or more data buses in order to facilitate processing of the data acquired.

Figure 5:
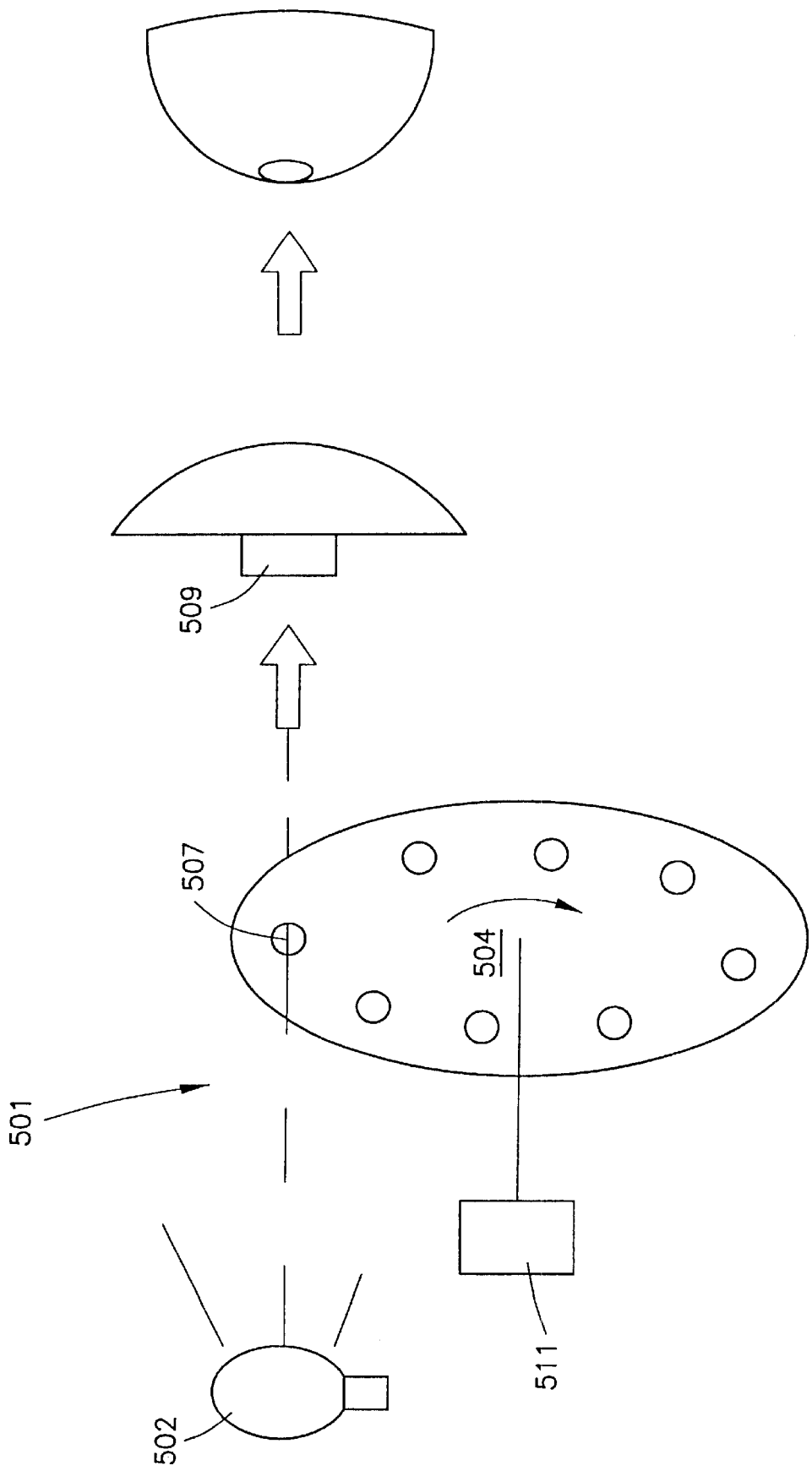
FIG. 5 is a schematic representation of a filter-type spectrometer.

FIG. 5 shows a monochromatic filter-type spectrometer 501, which utilizes a light source 502, such as the conventional light bulb shown in the figure to illuminate a rotating opaque circular disk 504, wherein the disk includes a number of narrow bandpass optical filters 507. The disk can be rotated so that each of the narrow bandpass filters passes between the light source and a sample 509. An encoder 511 controls which optical filter is presently under the light source. The filters 507 filter the light from the light source 502 so that only a narrow selected wavelength range passes through the filter to the sample 3. As illustrated in FIG. 5, the filter-type spectrometer 501 may be used with any one of the detectors described above in FIGS. 2–4.

Figure 6:
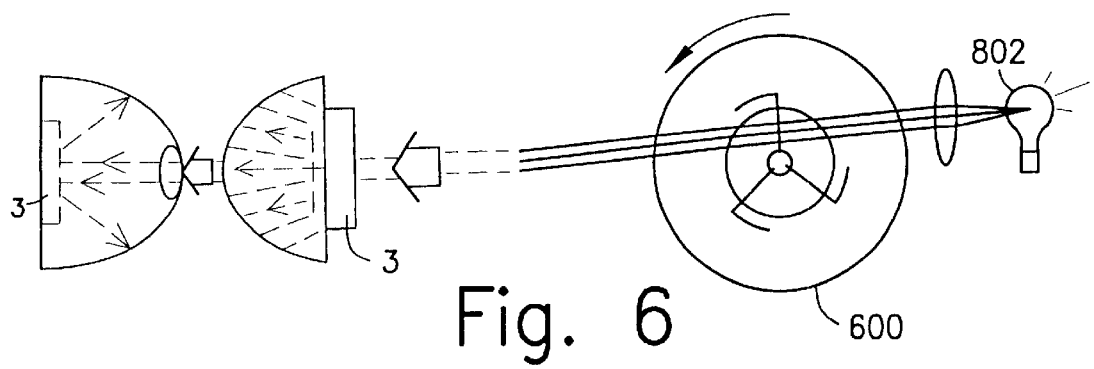
FIG. 6 shows a schematic representation of a rotating tilting filter wheel utilizing wedge interference filters having a light blocking flag.
Figure 7:
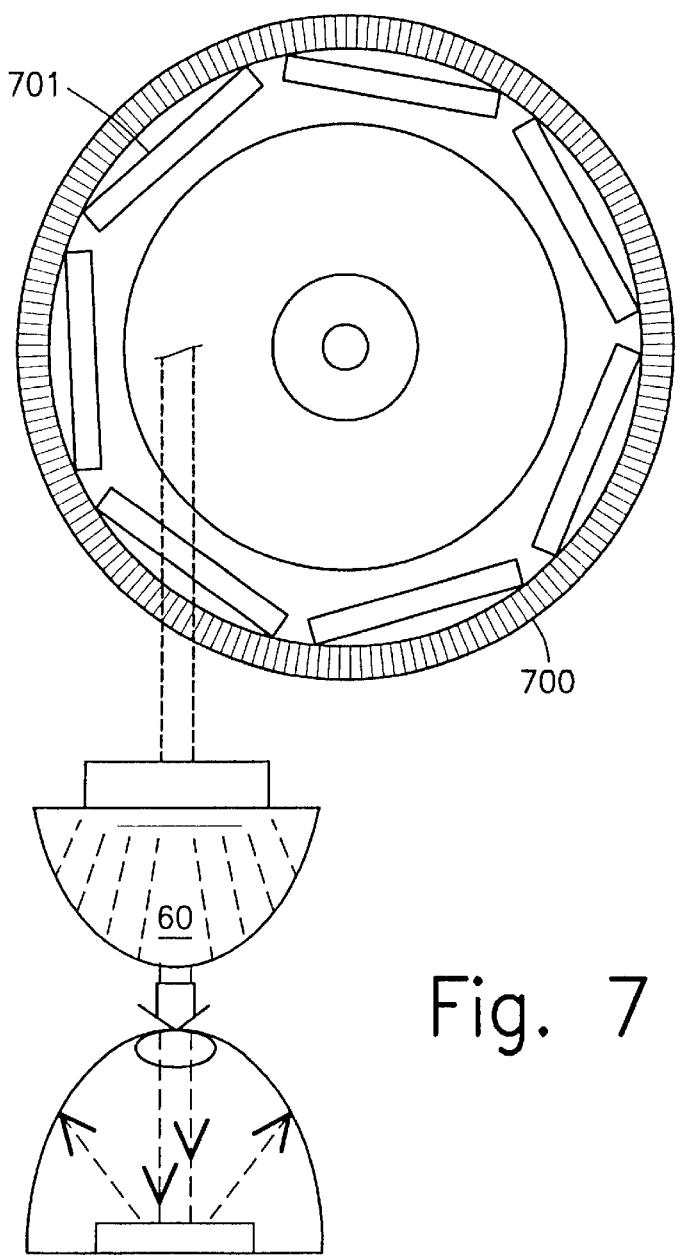
FIG. 7 shows a schematic representation of a spinning filter system in which the light passes through an encoder wheel.

FIGS. 6 and 7 illustrate two basic forms of filter-type NIR spectrophotometers utilizing a tilting filter concept.

FIG. 6 shows a rotating tilting filter wheel utilizing wedge interference filters having a light blocking flag. Light is transmitted from the light source 502 through the filter wheel 600 at varying wavelengths and bandpasses which is dependent on the incident angle of the light passing through the interference filter wedge to the sample.

FIG. 7 shows a spinning filter system in which the light passes through an encoder wheel 700, having a plurality of interference filters 701, to the sample 3. The spinning filter system operates using the same basic principle as the tilting filter of FIG. 6, but the interference filters 701 of the spinning filter system are mounted in an encoder wheel 700 for greater positioning accuracy (wavelength reproducibility) and greater reliability. As illustrated in FIGS. 6 and 7, the rotatable tilting filter wheel and spinning filter system may be used with any one of the detectors described above in FIGS. 2–4.

Figure 8:
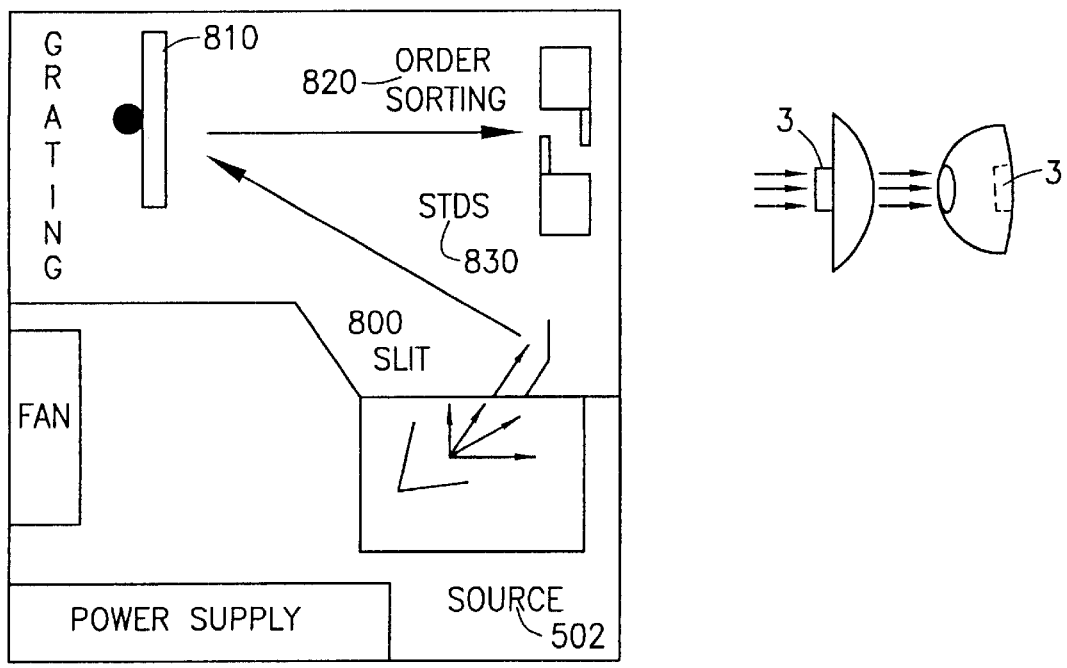
FIG. 8 shows a schematic representation of a typical pre-dispersive monochrometer-based instrument.

FIG. 8 shows a typical pre-dispersive monochrometer-based instrument where the light is dispersed prior to striking the sample. Referring to FIG. 8, the light source 502 transmits a beam of light through an entrance slit 800 and onto a grating 810. The grating 810 separates the light into a plurality of beams of different wavelengths. Via the order sorting 820 (to eliminate undesired wavelengths) and stds 830 (to provide a wavelength standard for calibration) components, a desired band of wavelengths is selected for transmission to the sample 3. As illustrated, this spectrometer may also be used with any one of the detectors described above in FIGS. 2–4.

Figure 9:
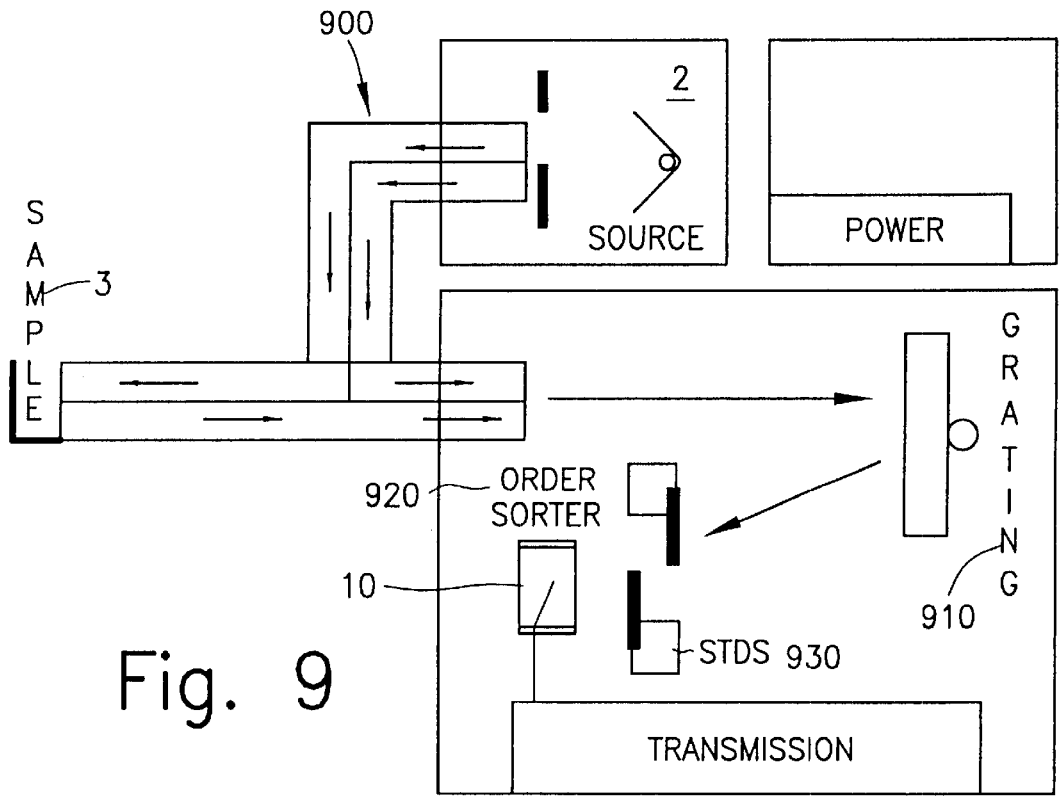
FIG. 9 shows a schematic representation of a post-dispersive monochrometer-based instrument.

FIG. 9 shows a typical post-dispersive monochrometer. This type of instrument provides the advantage of allowing the transmission of more energy on the sample via either a single fiberoptic strand or a fiberoptic bundle. Referring to FIG. 9, white light is transmitted through the fiberoptic strand or fiberoptic bundle 900 and onto the sample 3. The light is then reflected off of the sample 3 and back to the grating 910 (the dispersive element). After striking the grating 910 the light is separated into the various wavelengths prior to striking a detector. The post-dispersive monochrometer can be used with the reflectance detectors of FIGS. 2(a–d) or of FIGS. 4(a–e)(with the first portion 200 secured to the second portion 205). It should be noted that in this case, the detectors detect a reflectance spectrum rather than a transmittance spectrum.

Figure 10:
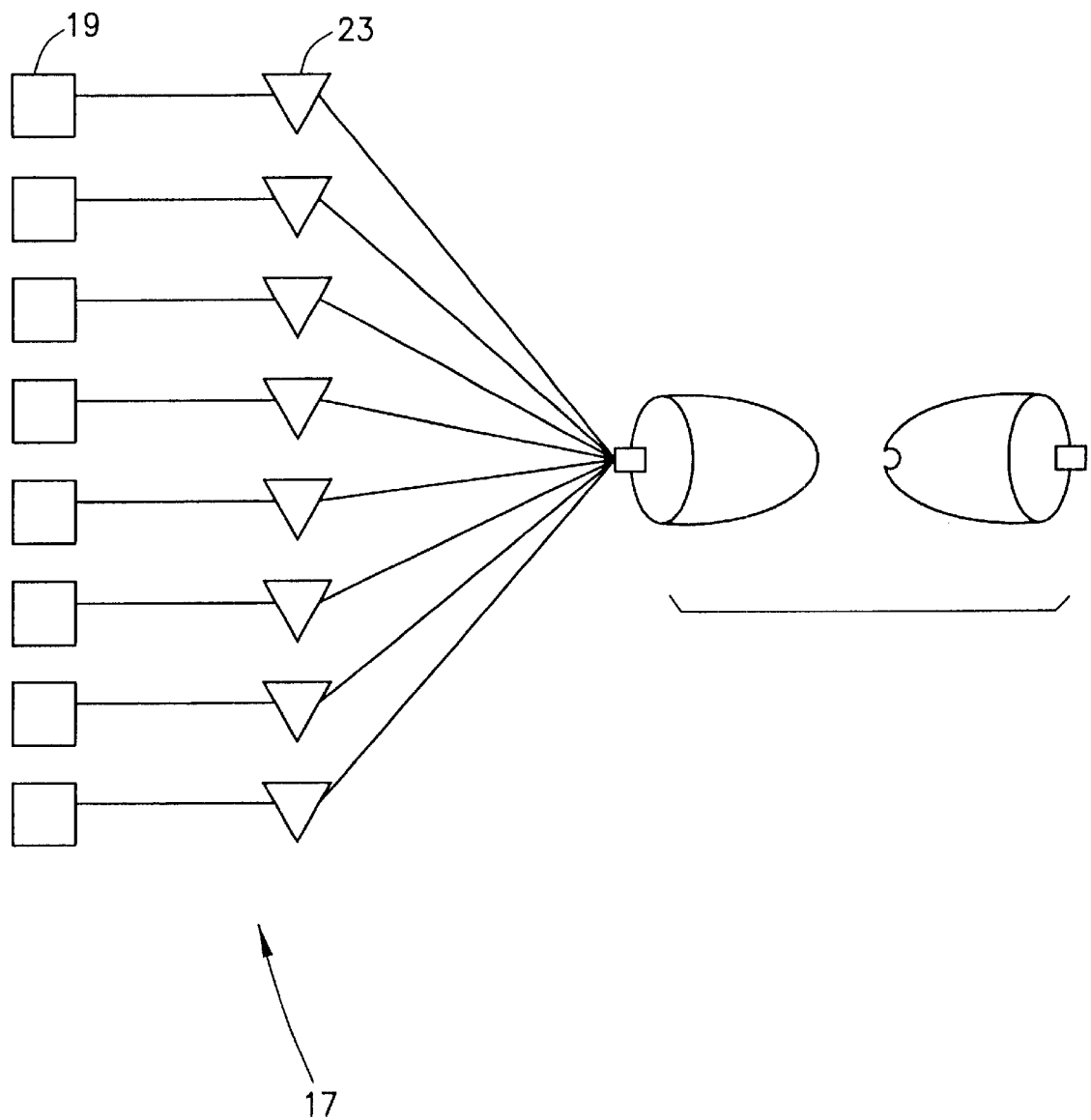
FIG. 10 is a schematic diagram of a Multiple discrete wavelength source spectrometer which uses infrared emitting diodes (IREDS) as a source of near-infrared radiation.

FIG. 10 is a diagram of a Multiple discrete wavelength source Spectrometer 17, which uses infrared emitting diodes (IREDs) as a source of near-infrared radiation. A plurality (for example, eight) of IREDs 19 are arranged over a sample work surface to be illuminated for quantitative analysis. Near-infrared radiation emitted from each IRED impinges upon an accompanying optical filter 23. Each optical filter is a narrow bandpass filter which passes NIR radiation at a different wavelength. As illustrated, this spectrometer may be used with any one of the detectors described above in FIGS. 2–4.

Figure 11:
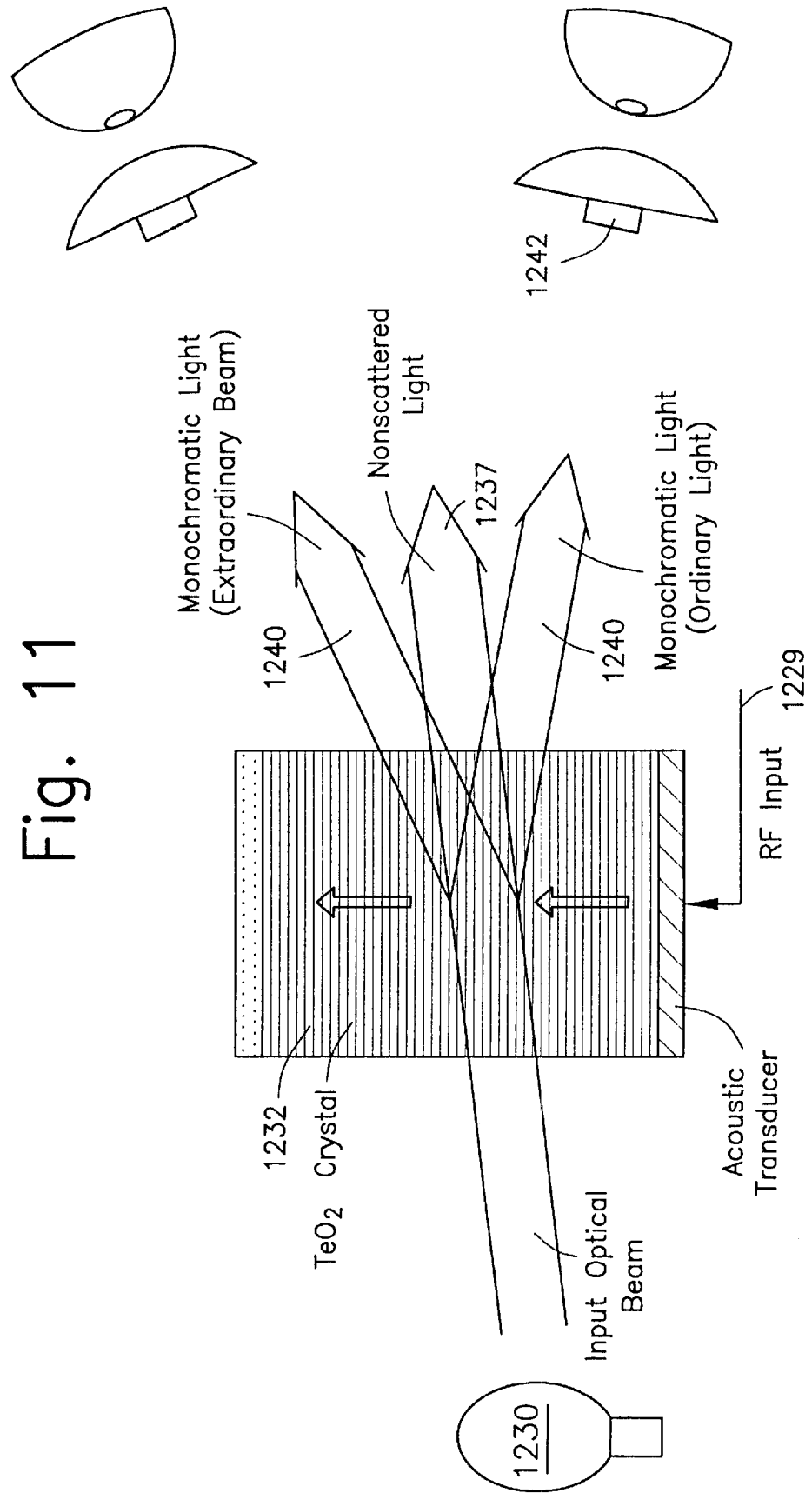
FIG. 11 shows a schematic diagram of an Acousto Optic Tunable Filter spectrometer.

FIG. 11 depicts an Acousto Optic Tunable Filter spectrometer utilizing an RF signal 1229 to generate acoustic waves in a $TeO_2$ crystal 1232. A light source 1230 transmits a beam of light through the crystal 1232, and the crystal splits the beam of light into three beams: a center beam of unaltered white light 1237 and two beams of monochromatic and orthogonally polarized light 1240. A sample 1242 is placed in the path of one of the monochromatic beams. The wavelength of the monochromatic light can be incremented across a wavelength band of interest by varying the RF frequency. As illustrated, this spectrometer may also be used with any one of the detectors described above in FIGS. 2–4.

Figure 12:
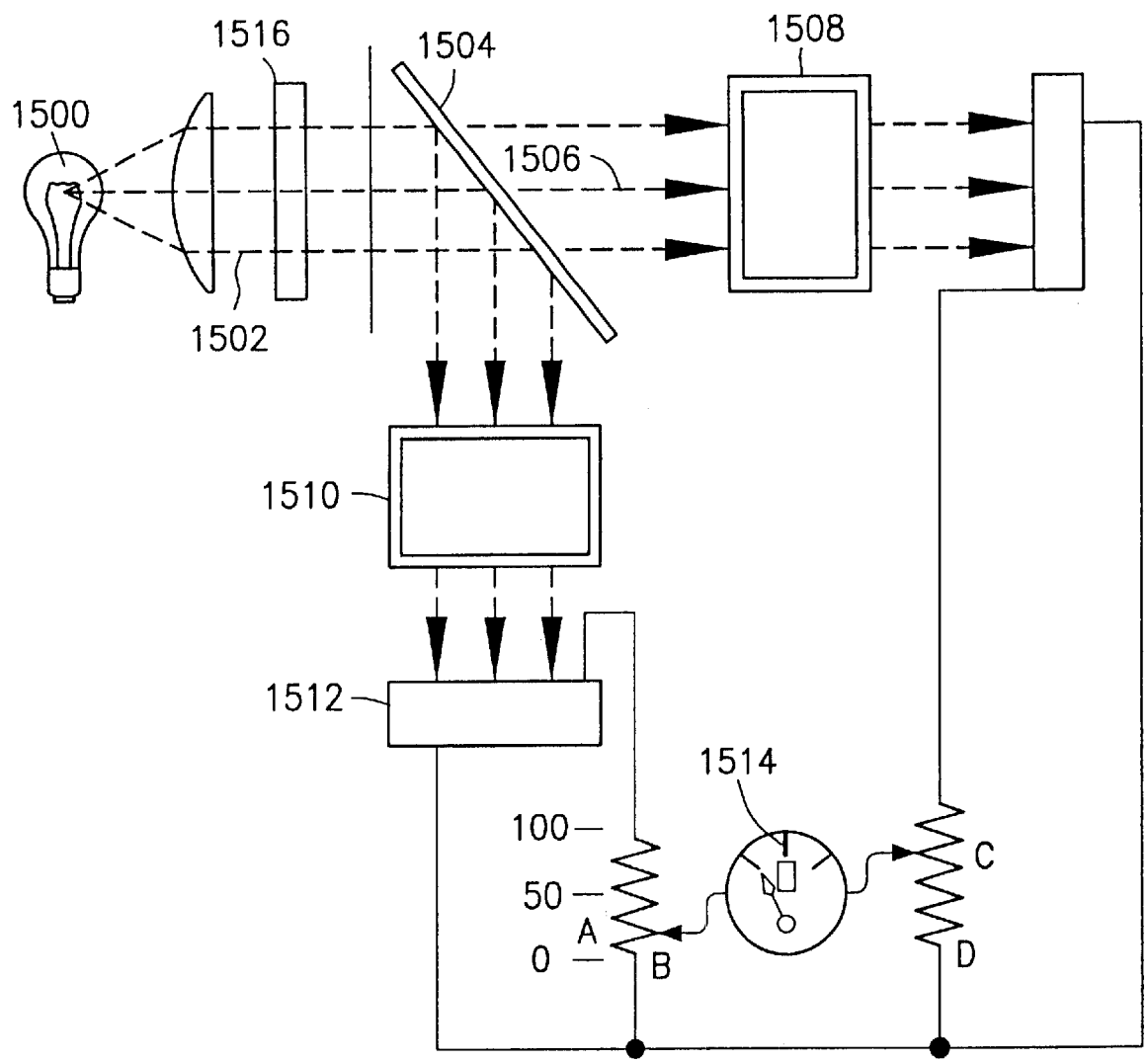
FIG. 12 is a schematic representation of a Double-Beam Spectrometer.

FIG. 12 depicts a Double Beam spectrometer. The Double Beam Spectrometer uses a light emitting source 1500, e.g., a tungsten lamp, to produce a beam 1502 of light which is split into two parts by a beam splitting device 1504, e.g., a half-silvered mirror, after passing through a filter device 1516. The first beam half 1506 passes through a sample 1508, which is placed in the path of one of the beams. The second beam half passes through a reference 1510. Detectors 1512, which may be any of the detectors described above in FIGS. 2–4, detect the radiation either transmitted through or reflected from the sample 1508 and reference 1510. Next, a null detector 1514 compares the results from both detectors and sends an electrical code corresponding to whether the results from both detectors are the same or different. This allows a chart corresponding to different wavelengths to be constructed.

Figure 13:
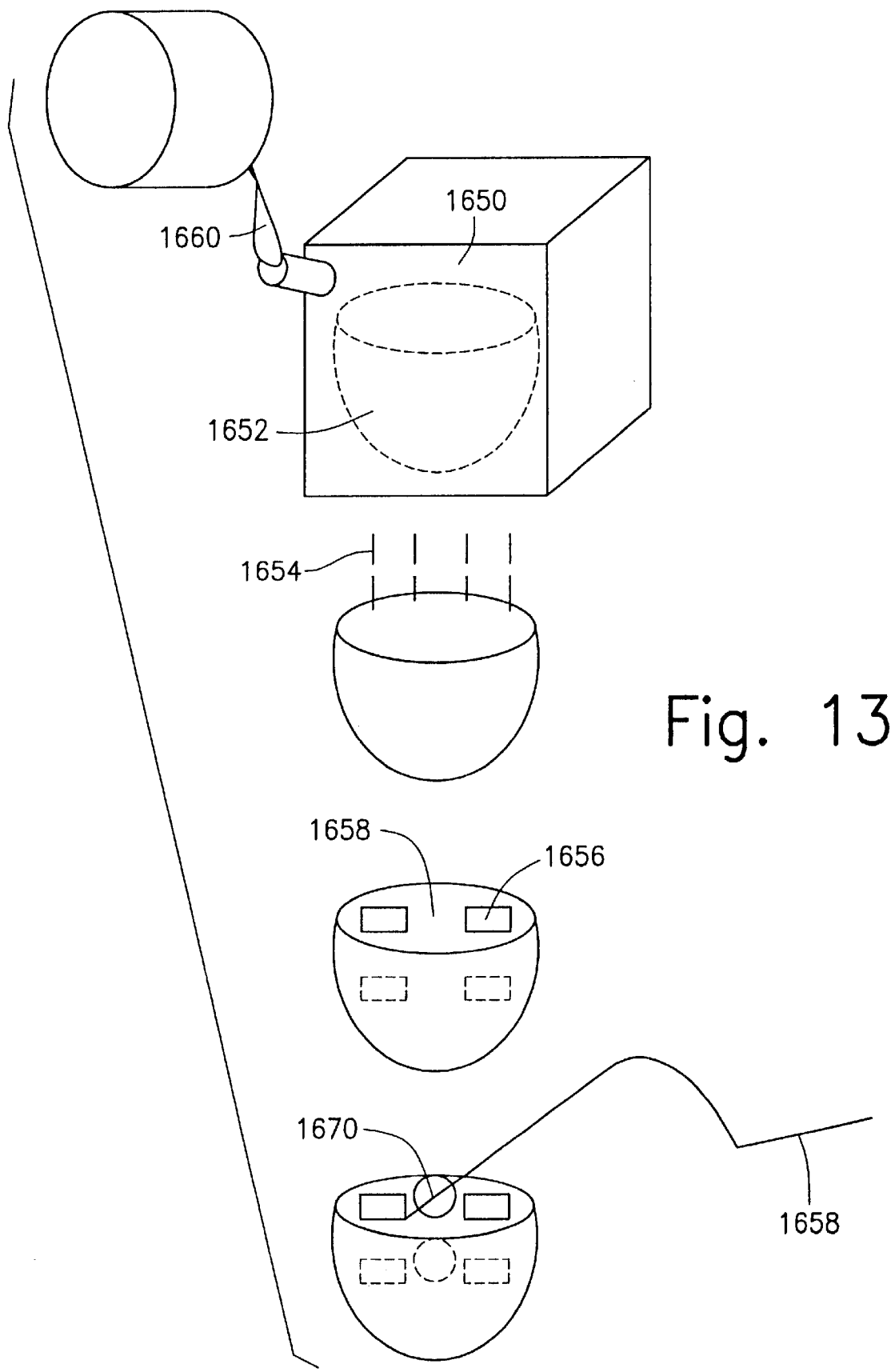
FIG. 13 is a schematic diagram of a ceramic mold method of construction of the detector.

FIG. 13 depicts a Mold method of constructing a hemispherical detector in accordance with the present invention. A press mold 1650 is made to resemble the desired shape of the hemispherical detector. A material 1660, e.g., plastic, that is a liquid at a high temperature and a solid at a lower temperature is poured into the press mold 1650 to form a cast 1652. After the mold has set, the cast 1652 is removed from the press mold 1650. Next, the cast 1652 is finished, e.g., sanded, to remove any defects caused by the process and then coated by a coating material 1654 designed to preserve the material. A plurality of photdetectors 1656 are then attached to the inner surface 1658 of the cast 1652 so as to form a substantially contiguous array. Apertures 1670 may be drilled through the cast 1652, in order to facilitate the attachment of wires 1658 to the photodetectors 1656. Alternatively, the mold 1650 itself could be configured to provide the apertures 1670.

Figure 14:
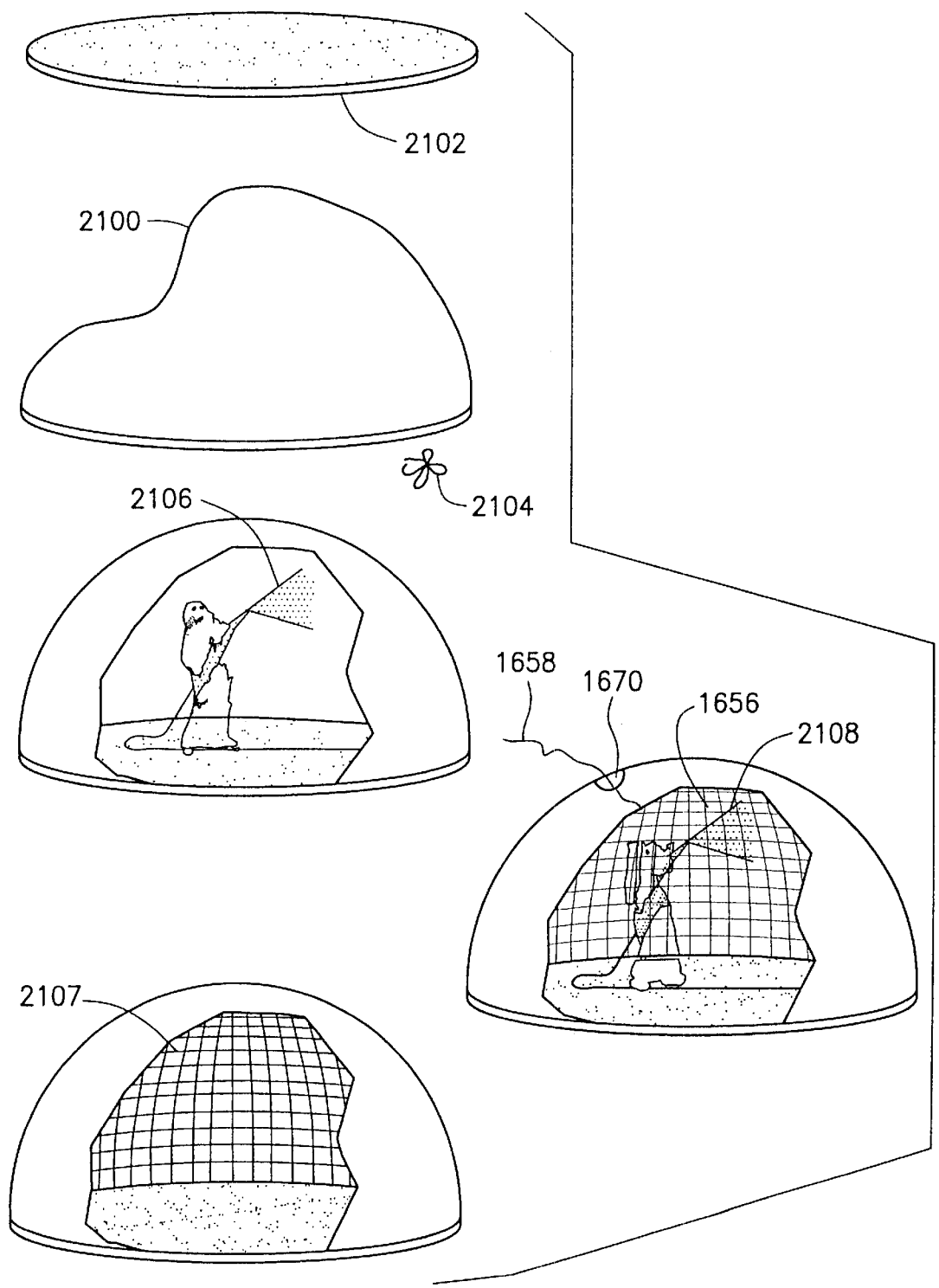
FIG. 14 is a schematic diagram of a malleable airform method of construction of the detector.

FIG. 14 depicts an Airform method for constructing a hemispherical detector in accordance with the present invention. A malleable airform 2100, e.g., plastic, is fabricated to the proper shape and size. The malleable airform 2100 is placed on a ring base 2102 and inflated with a blower fan 2104. A hardening material 2106, e.g., polyurethane foam, is then applied to the interior surface of the malleable airform 2100 to stabilize the hemispherical structure. After the hardening material 2106 has set, a plurality of reinforcing bars 2107, e.g., plastic, may be attached to the hardening material 2106 in order to stabilize the hardening material 2106. A second layer of hardening material 2108 may be applied to the interior surface 2110 of the reinforcing bars 2107 in order to further stabilize it. After the second of hardening material 2108 has hardened, a plurality of photodetectors 1656 arranged in a substantially contiguous array are attached to the second layer of hardening material 2106 to form the hemispherical detector. Apertures 1670 may be drilled through the hardening material 2106, in order to facilitate the attachment of wires 1658 to the photodetectors 1656.

Figure 15:
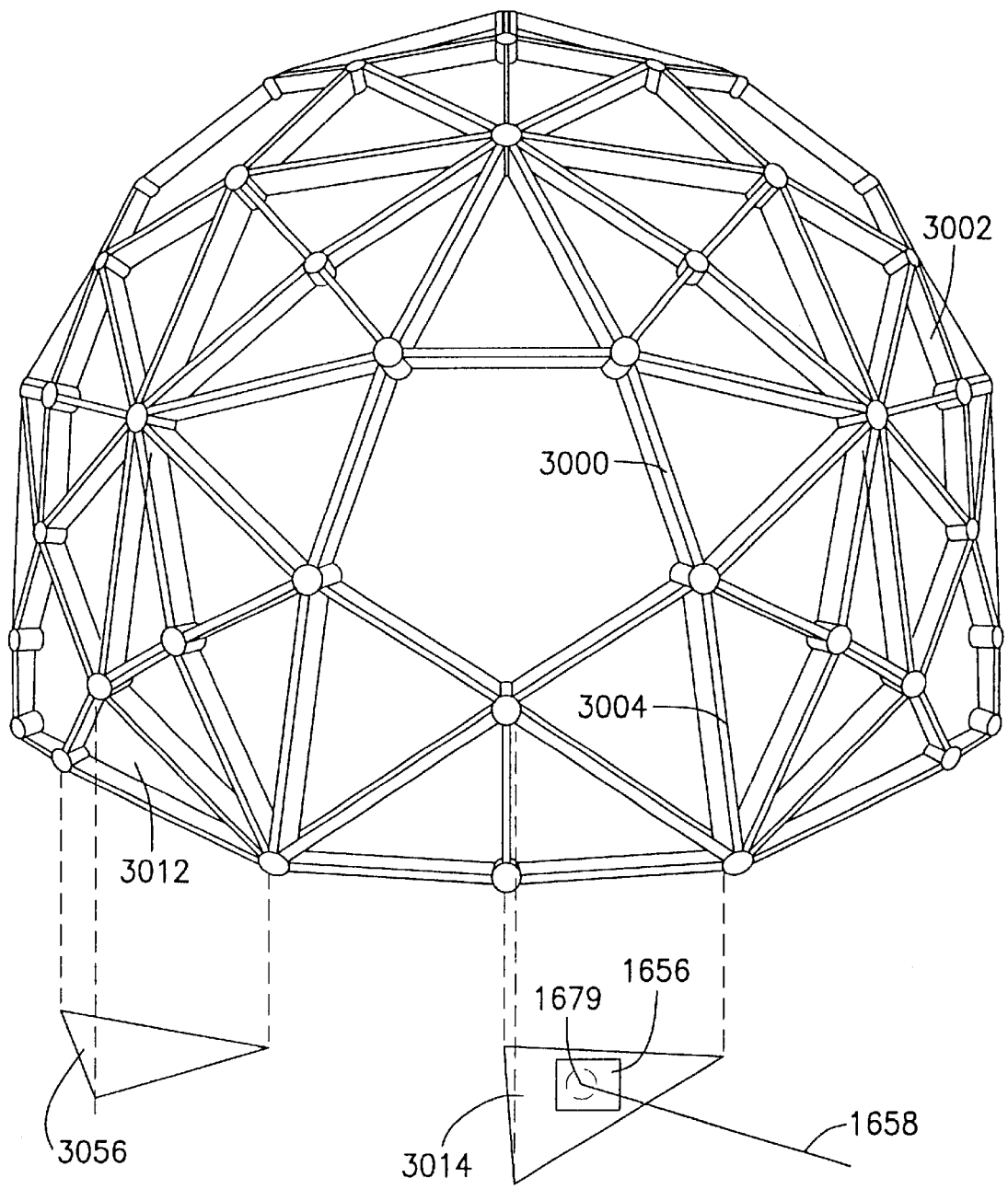
FIG. 15 is a schematic diagram of geodesic dome method of construction of the detector.

FIG. 15 depicts a geodesic dome method for constructing a hemispherical detector in accordance with the present invention. A plurality of pentagons 3000, hexagons 3002, and half hexagons 3004 are assembled from a plurality of sufficiently sturdy small struts 3006, e.g., hardened plastic. Alternatively, the pentagons 3000, hexagons 3002, and half-hexagons 3004 could be pre-formed (e.g., molded plastic). In any event, the pentagons 3000, hexagons 3002, and half hexagons 3004 are then joined together in a geodesic dome shape, e.g., such that every pentagon is surrounded by 5 hexagons 3002, half-hexagons 3004, or combination thereof. A plurality of fitted photodetectors 3056 shaped to fit in a plurality of areas 3012 between the small struts 3006 may then be secured to said areas 3012 by a mechanical, e.g., screws, or a static, e.g., glue, material so as to form a substantially contiguous array. Another option is to fit a plurality of fillings 3014 shaped to fit in the areas 3012 between the small struts 3006 and then secure the fillings 3014 to the areas by a mechanical, e.g., screws, or non-mechanical, e.g., glue, material. Photodetectors 1656 may then be attached in a substantially contiguous array to the fillings by a mechanical, e.g., screws, or static, e.g., glue, material to form a hemispherical detector. Also, a plurality of fitted photodetectors 3056 may fill a portion of the areas, as detailed above, and then the remaining areas may be filled with a plurality of fillings 3014, also detailed above, which may then have photodetectors attached, so as to form a substantially contiguous array. Apertures 1670 may be drilled through the fillings 3014, in order to facilitate the attachment of wires 1658 to the photodetectors 1656. Alternatively, the wires 1658 may be attached directly to the back of the fitted photdetectors 3056.

What is claimed is:

1. A detector comprising:
   a plurality of photodetectors arranged in a substantially contiguous array forming an interior surface of the detector substantially in the shape of a half-sphere and the half-sphere defining a closed end and an open end, the open end defining a substantially circular face.

2. A detector according to claim 1 further comprising a NIR filter-type spectrometer which utilizes a light source such to illuminate a rotating opaque disk.

3. A detector according to claim 1 further comprising a near IR spectrometer that utilizes a tilting filter wheel.

4. A detector according to claim 1 further comprising a near IR spectrometer utilizing interference filters mounted in an encoder wheel.

5. A detector according to claim 1 further comprising a NIR pre-dispersive monochrometer-based instrument where the light is dispersed prior to striking the sample.

6. A detector according to claim 1 further comprising a NIR post-dispersive monochrometer using a fiberoptic strand or bundle.

7. A detector according to claim 1 further comprising a NIR multiple discrete wavelength source spectrometer utilizing infrared emitting diodes as a source of near-infrared radiation.

8. A detector according to claim 1 further comprising an NIR Acousto Optic Tunable Filter spectrometer utilizing an RF signal to generate acoustic waves in a TeO2 crystal.

9. A detector according to claim 1 further comprising a NIR double beam spectrometer utilizing a beam splitting device.

10. The detector as recited in claim 1 wherein the photodetectors are photoconductive photon detectors.

11. The detector as recited in claim 10, wherein the photoconductive photon detectors are selected from the group consisting of PbSi photoconductive photon detectors, PbSe photon detectors, InAs photon detectors, and InGaAs photon detectors.

12. The detector as recited in claim 1 wherein the photodetectors are selected from the group consisting of photovoltaic photon detectors, InSb photon detectors, photodiodes, photoconductive cells, and HgCdTe photoconductive detectors.

13. The detector as recited in claim 1 wherein the photodetectors are selected from the group consisting of Ge detectors, Si detectors, and PbS detectors.

14. The detector as recited in claim 1 wherein the substantially circular face has a diameter of from about 1.5 mm to about 1 m.

15. The detector as recited in claim 1 wherein the array includes at least two different types of photodetectors.

16. A detector comprising a plurality of photodetectors arranged in a substantially contiguous array forming an interior surface of the detector substantially in the shape of a truncated half-sphere and defining a first open end and a second open end, the second open end defining a substantially circular face having a diameter ("d"), the first open end having a cutout formed therein, wherein the cutout defines an area which is less than $\Pi (d/2)^2$.

17. A detector according to claim 16 further comprising a NIR filter-type spectrometer which utilizes a light source such to illuminate a rotating opaque disk.

18. A detector according to claim 16, further comprising a near IR spectrometer that utilizes a tilting filter wheel.

19. A detector according to claim 16 further comprising a near IR spectrometer utilizing interference filters mounted in an encoder wheel.

20. A detector according to claim 16 further comprising a NIR pre-dispersive monochrometer-based instrument where the light is dispersed prior to striking the sample.

21. A detector according to claim 16 further comprising a NIR post-dispersive monochrometer using a fiberoptic strand or bundle.

22. A detector according to claim 16 further comprising a NIR multiple discrete wavelength source spectrometer utilizing infrared emitting diodes as a source of near-infrared radiation.

23. A detector according to claim 16 further comprising an NIR Acousto Optic Tunable Filter spectrometer utilizing an RF signal, to generate acoustic waves in a TeO2 crystal.

24. A detector according to claim 16 further comprising a NIR double beam spectrometer utilizing a beam splitting device.

25. The detector as recited in claim 16 wherein the photodetectors are photoconductive photon detectors.

26. The detector as recited in claim 25 wherein the photoconductive photon detectors are selected from the group consisting of PbSi photoconductive photon detectors, PbSe photon detectors, InAs photon detectors, and InGaAs photon detectors.

27. The detector as recited in claim 16 wherein the photodetectors are selected from the group consisting of photovoltaic photon detectors, InSb photon detectors, photodiodes, photoconductive cells, and HgCdTe photoconductive detectors.

28. The detector as recited in claim 16 wherein the photodetectors are selected from the group consisting of Ge detectors, Si detectors, and PbS detectors.

29. The detector as recited in claim 16 wherein the substantially circular face has a diameter of from about 1.5 mm to about 1 m.

30. The detector as recited in claim 16 wherein the array includes at least two different types of photodetectors.

31. A detector comprising a plurality of photodetectors arranged in a substantially contiguous array forming an interior surface of the detector substantially in the shape of a half-sphere and includes a first portion and a second portion, the first portion being in the shape of a truncated half sphere, the truncated half sphere defining a first open end and a second open end, the second open end defining a substantially circular face having a diameter ("d"), the first open end having a cutout formed therein, wherein the cutout defines an area which is less than $\Pi (d/2)^2$, the second portion being removably secured to the first open end, the second portion covering the cutout when the second portion is secured to the first open end.

32. A detector according to claim 31 further comprising a NIR filter-type spectrometer which utilizes a light source such to illuminate a rotating opaque disk.

33. A detector according to claim 31 further comprising a near IR spectrometer that utilizes a tilting filter wheel.

34. A detector according to claim 31, further comprising a near IR spectrometer utilizing interference filters mounted in an encoder wheel.

35. A detector according to claim 31 further comprising a NIR pre-dispersive monochrometer-based instrument where the light is dispersed prior to striking the sample.

36. A detector according to claim 31 further comprising a NIR post-dispersive monochrometer using a fiberoptic strand or bundle.

37. A detector according to claim 31 further comprising a NIR multiple discrete wavelength source spectrometer utilizing infrared emitting diodes as a source of near-infrared radiation.

38. A detector according to claim 31 further comprising an NIR Acousto Optic Tunable Filter spectrometer utilizing an RF signal to generate acoustic waves in a TeO2 crystal.

39. A detector according to claim 31 further comprising a NIR double beam spectrometer utilizing a beam splitting device.

40. The detector as recited in claim 31 wherein the photodetectors are photoconductive photon detectors.

41. The detector as recited in claim 40 wherein the photoconductive photon detectors are selected from the group consisting of PbSi photoconductive photon detectors, PbSe photon detectors, InAs photon detectors, and InGaAs photon detectors.

42. The detector as recited in claim 31 wherein the photodetectors are selected from the group consisting of photovoltaic photon detectors, InSb photon detectors, photodiodes, photoconductive cells, and HgCdTe photoconductive detectors.

43. The detector as recited in claim 31 wherein the photodetectors are selected from the group consisting of Ge detectors, Si detectors, and PbS detectors.

44. The detector as recited in claim 31 wherein the substantially circular face has a diameter of from about 1.5 mm to about 1 m.

45. The detector as recited in claim 31 wherein the array includes at least two different types of photodetectors.

\* \* \* \* \*